(12) United States Patent
Kim et al.

(10) Patent No.: US 12,329,860 B2
(45) Date of Patent: Jun. 17, 2025

(54) HYALURONIC ACID-BASED DISSOLVING FILM, PRODUCTION METHOD THEREOF, AND RELEASE LINER USED FOR THE SAME

(71) Applicant: GENEWEL CO., LTD., Gyeonggi-do (KR)

(72) Inventors: Jun Ho Kim, Gyeonggi-do (KR); Mi Ran Cho, Gyeonggi-do (KR); Hye Ri Lee, Daejeon (KR)

(73) Assignee: GENEWEL CO., LTD. (KR)

( * ) Notice: Subject to any disclaimer, the term of this patent is extended or adjusted under 35 U.S.C. 154(b) by 782 days.

(21) Appl. No.: 17/601,881

(22) PCT Filed: Apr. 10, 2020

(86) PCT No.: PCT/KR2020/004866
§ 371 (c)(1),
(2) Date: Oct. 6, 2021

(87) PCT Pub. No.: WO2020/209654
PCT Pub. Date: Oct. 15, 2020

(65) Prior Publication Data
US 2022/0202734 A1 Jun. 30, 2022

(30) Foreign Application Priority Data
Apr. 10, 2019 (KR) .................. 10-2019-0041700

(51) Int. Cl.
| | |
|---|---|
| C09J 7/40 | (2018.01) |
| A61K 9/70 | (2006.01) |
| A61K 47/10 | (2017.01) |
| A61K 47/32 | (2006.01) |
| A61K 47/36 | (2006.01) |
| A61K 47/38 | (2006.01) |
| C08J 5/18 | (2006.01) |
| C08L 5/08 | (2006.01) |
| C09J 131/04 | (2006.01) |

(52) U.S. Cl.
CPC ............ *A61K 9/7007* (2013.01); *A61K 47/10* (2013.01); *A61K 47/32* (2013.01); *A61K 47/36* (2013.01); *A61K 47/38* (2013.01); *C08J 5/18* (2013.01); *C08L 5/08* (2013.01); *C09J 7/401* (2018.01); *C09J 131/04* (2013.01); *C08J 2305/08* (2013.01); *C08L 2203/02* (2013.01); *C09J 2431/00* (2013.01); *C09J 2467/005* (2013.01)

(58) Field of Classification Search
CPC ...... A61K 9/7007; A61K 47/10; A61K 47/32; A61K 47/36; A61K 47/38; C09J 7/401; C09J 131/04; C09J 2431/00; C09J 2467/005; C08J 5/18; C08J 2305/08; C08L 5/08; C08L 2203/02
See application file for complete search history.

(56) References Cited

U.S. PATENT DOCUMENTS

| | | | | |
|---|---|---|---|---|
| 5,891,078 | A | * | 4/1999 | Turngren ............ A61F 13/0279 602/57 |
| 2010/0310631 | A1 | * | 12/2010 | Domard ................ A61K 47/36 424/85.4 |
| 2013/0183491 | A1 | * | 7/2013 | Fujisawa .............. B05D 3/0254 428/221 |
| 2017/0226298 | A1 | * | 8/2017 | Friedrich .................. B32B 1/00 |

FOREIGN PATENT DOCUMENTS

| | | | | | |
|---|---|---|---|---|---|
| EP | 3593973 | A1 | * | 1/2020 | ............ A61L 27/20 |
| JP | 2004510542 | A | | 4/2004 | |
| JP | 2011036622 | A | | 2/2011 | |
| JP | 2014114355 | A | | 6/2014 | |
| JP | 2018518500 | A | | 7/2018 | |
| KR | 10-2017-0024543 | A | | 3/2017 | |
| WO | WO-2015173547 | A1 | * | 11/2015 | ....... A61F 13/00008 |
| WO | WO-2019135438 | A1 | * | 7/2019 | ........... A61K 8/0208 |

OTHER PUBLICATIONS

English translation of WO2019135438 from Google Patents. Retrieved on Oct. 18, 2024, 3 pages. (Year: 2024).*
International Search Report for PCT/KR2020/004866 dated Jul. 20, 2020, 10 pages (including the English translation).

* cited by examiner

*Primary Examiner* — Doan T Phan
(74) *Attorney, Agent, or Firm* — Quarles & Brady LLP

(57) ABSTRACT

The present invention relates to a hyaluronic acid-based dissolving film, a production method thereof, and a release liner used for the same, and more particularly to a method for producing a hyaluronic acid-based dissolving film that provides a hyaluronic acid-based dissolving film having high performance with high productivity through a continuous production process to allow mass production of the dissolving film, a hyaluronic acid-based dissolving film produced by the method, and a release liner suitable for the dissolving film.

6 Claims, 5 Drawing Sheets

[FIG. 1]
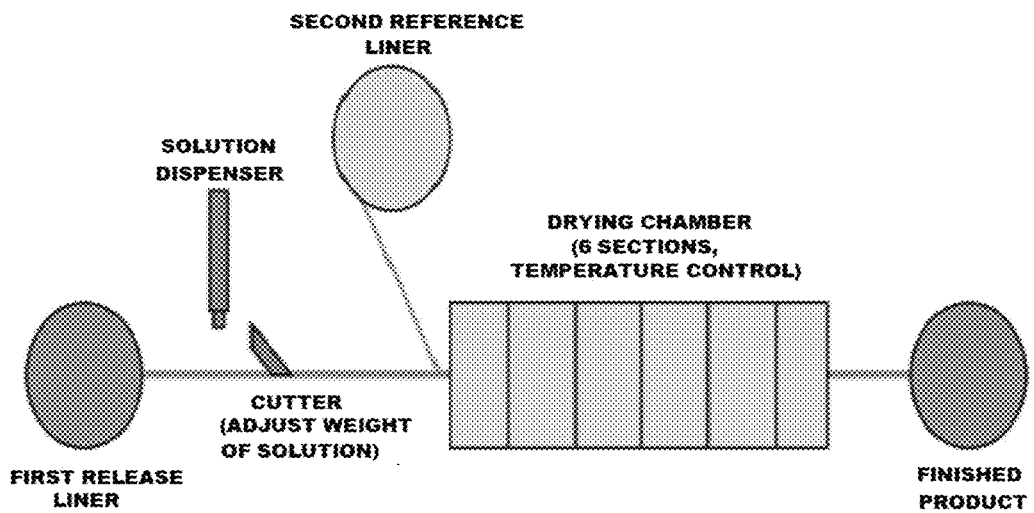
[FIG. 2]
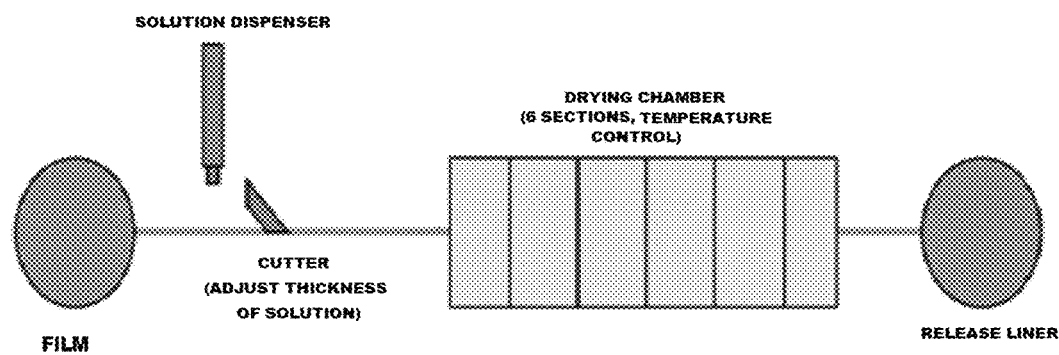

[FIG. 5]
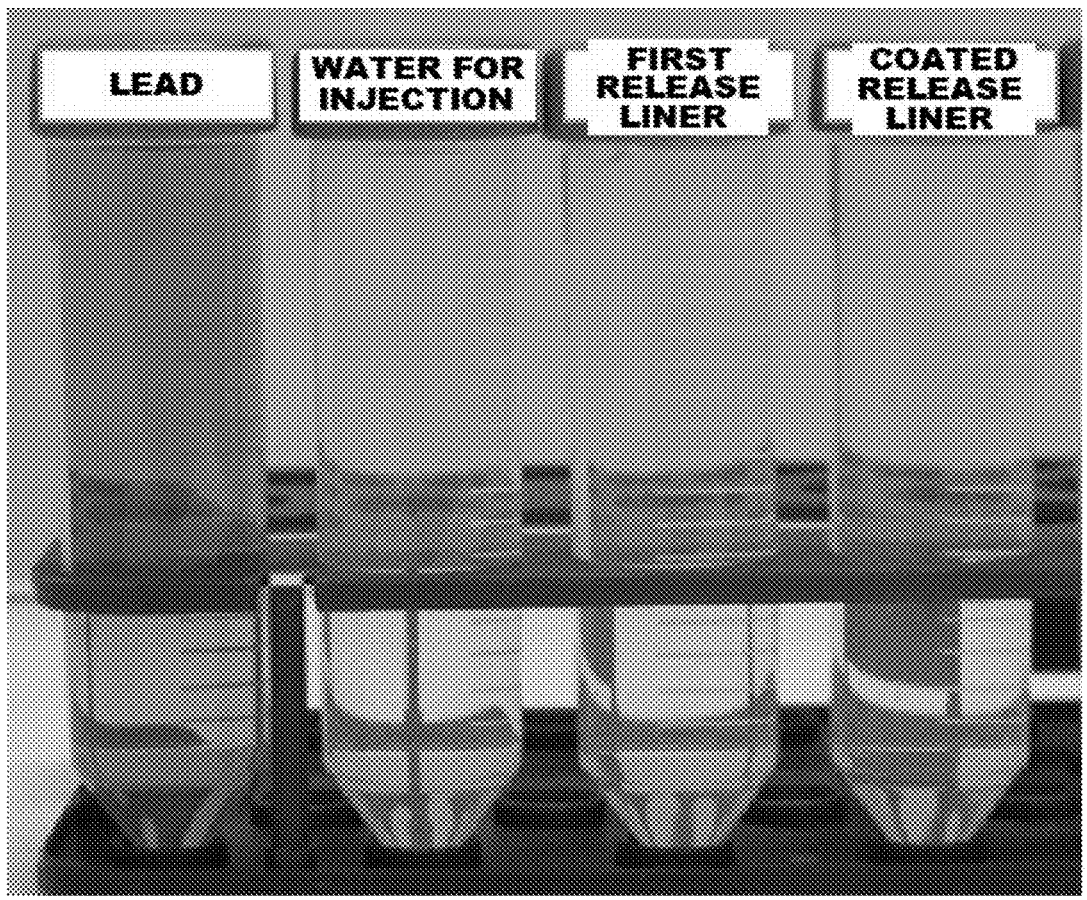

[FIG. 6]
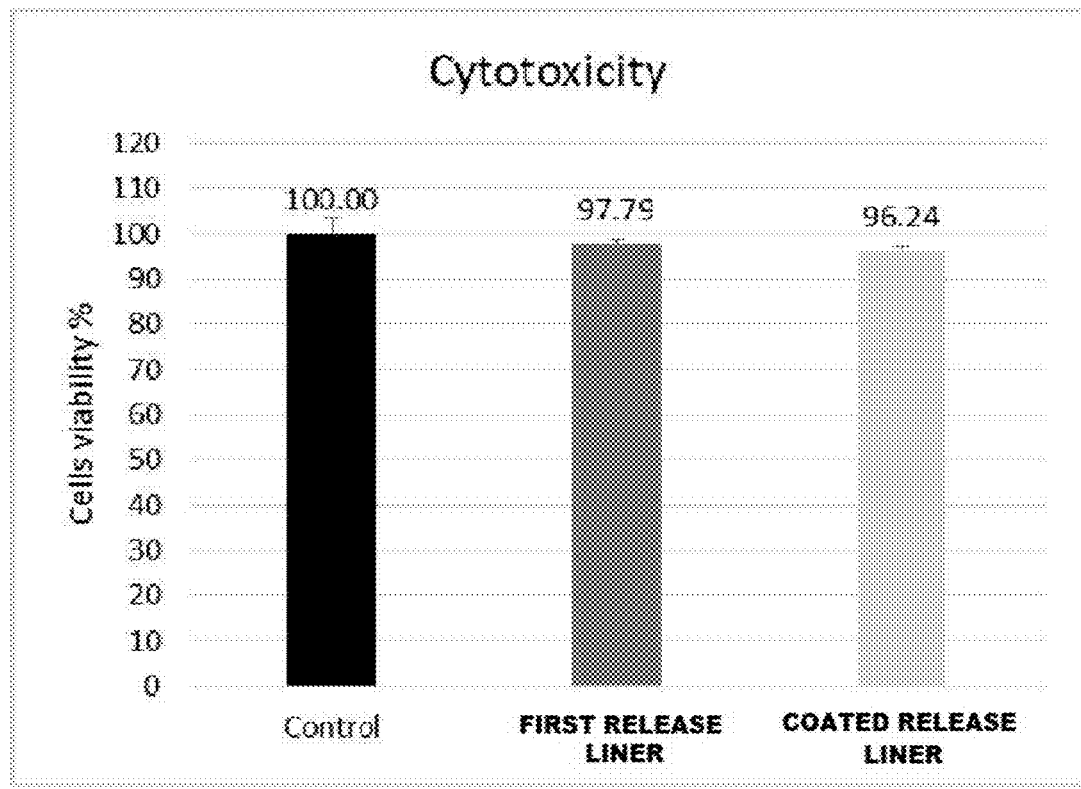

HYALURONIC ACID-BASED DISSOLVING FILM, PRODUCTION METHOD THEREOF, AND RELEASE LINER USED FOR THE SAME

CROSS-REFERENCE TO RELATED APPLICATIONS

This application claims priority to and is a 35 U.S.C. § 371 national phase application of PCT/KR2020/004866 (WO2020/209654), filed on Apr. 10, 2020, entitled "HYALURONIC ACID-BASED DISSOLVING FILM, METHOD FOR PRODUCING SAME AND RELEASE SHEET USED THEREFOR", which application claims priority to and the benefit of Korean Application No. 10-2019-0041700, filed on Apr. 10, 2019, the disclosures of which are incorporated herein by reference in their entirety.

TECHNICAL FIELD

The present invention relates to a hyaluronic acid-based dissolving film, a production method thereof, and a release liner used for the same, and more particularly to a method for producing a hyaluronic acid-based dissolving film that provides a hyaluronic acid-based dissolving film having high performance with high productivity through a continuous production process to allow mass production of the dissolving film, a hyaluronic acid-based dissolving film produced by the method, and a release liner suitable for the dissolving film.

BACKGROUND ART

Hyaluronic acid (HA) improves the moisturizing ability of the skin, maintains the elasticity of the skin, reduces the damage to the lower layer of the skin when the skin is damaged, and acts as a lubricant to facilitate the movement of collagen, the main component of the skin, between cells. It also has an important action on the skin as a substance highly hydrophilic as much as can be called a natural moisturizer. Besides, it has a function as a moisturizing factor with its high-water retention thanks to many hydroxyl groups (—OH) in the molecule and serves as a biocompatible material that inhibits the penetration of external substances such as bacteria to prevent diseases like skin infections.

Conventionally, powdery hyaluronic acid is inconvenient to use as it releases flying powder, and liquid hyaluronic acid is difficult to produce industrially due to its high hygroscopicity that causes microbial contamination and consequently deterioration. In order to solve this problem, a method of preparing hyaluronic acid in the form of a film has been proposed. Yet, the conventional hyaluronic acid film is manufactured by casting a hyaluronic acid-based solution on a tray and drying it out for a long time in an oven or a chamber with a thermo-hydrostat. Thus, its production method leads to low productivity and hence difficulty in mass production of the film. In addition, the conventional hyaluronic acid film is easy to tear and break in the process of manufacturing and transport, and even before the use. Despite a release liner used to compensate for this weakness, the adhesion of the hyaluronic acid film to the release liner is too weak to acquire the complementary effect, unavoidably making the hyaluronic acid film loose and causing inconvenience to both producers and consumers.

PRIOR ART DOCUMENTATION

Patent Document (Patent Document 1) KR Patent No. 2018-0102735

SUMMARY OF THE DISCLOSURE

For solving the above-mentioned problems with the prior art, it is an object of the present invention to provide a high-performance hyaluronic acid-based dissolving film with high productivity by preparing a hyaluronic acid-based solution of a specific composition that can be carried on a continuous production line and producing a hyaluronic acid-based dissolving film through a continuous production process using the hyaluronic acid-based solution.

It is another object of the present invention to provide a release paper that is excellent in both adhesion and detachability with the hyaluronic acid-based dissolving film and hence suitable to produce the hyaluronic acid-based dissolving film of the present invention.

The above and other objects of the present invention can be all achieved by the present invention described as follows.

In order to achieve the objects, the present invention provides a continuous production method for a hyaluronic acid-based dissolving film that includes: preparing a hyaluronic acid-based solution capable of being carried on a continuous production line; supplying a release paper to the continuous production line; continuously applying the hyaluronic acid-based solution on the upper side of the release paper supplied to the continuous production line; and drying the applied hyaluronic acid-based solution on the continuous production line to form a hyaluronic acid-based dissolving film.

The term "continuous production line" as used in the present invention is not specifically limited so long as it refers to a continuous production line generally used in the related art of the present invention, and it may mean, for example, a continuous production process that flows without interruption from supplying a release paper to making the finished product or involves a release paper being supplied and continuously in motion to make the finished product.

The term "dissolving film" as used in the present invention refers to a film that readily dissolves in a solvent, such as water, cosmetic water (water- and/or oil-based), and ethanol to have its film form disappear and turn into a solution or emulsion.

The term "release paper" as used in the present invention is defined as a means that is adhered to the one side or both sides of the hyaluronic acid-based dissolving film to support, protect or transfer the hyaluronic acid-based dissolving film and removed before or after use. The release liner includes a release film, a release sheet, a release liner, separate paper, the like.

The method may further include applying a coating solution on the upper side of the release paper and then drying the applied coating solution, prior to or after the step of supplying the release paper to the continuous production line, where the coating solution includes at least one selected from the group consisting of polyvinyl alcohol, polyvinyl acetate, and polyvinyl pyrrolidone. In this case, the hyaluronic acid-based dissolving film is stably adhered to the release paper. This can eliminate an issue of inconvenience of the conventional dissolving film during use, such as releasing flying powder.

The coating solution may preferably include 10 to 45 wt. % of polyvinyl acetate, 0 to 20 wt. % of water, 20 to 70 wt. % of ethanol, 1 to 15 wt. % of polyvinyl pyrrolidone, and 0 to 40 wt. % of ethyl acetate; and more preferably, 15 to 45 wt. % of polyvinyl acetate, 0 to 20 wt. % of water, 25 to 65 wt. % of ethanol, 3 to 10 wt. % of polyvinyl pyrrolidone, and 0 to 35 wt. % of ethyl acetate. In the defined range of composition, it is possible not only to provide excellent adhesion with the hyaluronic acid-based dissolving film, making the release liner stick well to the film during and after production of the film, but also to ensure such a good detachability that the release liner can be easily removed by hand when being cut out.

As another example, the coating solution may preferably include 10 to 20 wt. % of polyvinyl acetate, 10 to 20 wt. % of water, 50 to 70 wt. % of ethanol, and 1 to 10 wt. % of polyvinyl pyrrolidone; and more preferably, 15 to 20 wt. % of polyvinyl acetate, 14 to 20 wt. % of water, 60 to 70 wt. % of ethanol, and 1 to 5 wt. % of polyvinyl pyrrolidone. In the defined range of composition, it is possible not only to provide excellent adhesion with the hyaluronic acid-based dissolving film, making the release liner stick well to the film during and after production of the film, but also to ensure such a good detachability that the release liner can be easily removed by hand when being cut out.

As further another example, the coating solution may preferably include 20 to 40 wt. % of polyvinyl acetate, 20 to 45 wt. % of ethanol, 5 to 15 wt. % of polyvinyl pyrrolidone, and 20 to 40 wt. % of ethyl acetate; and more preferably, 25 to 35 wt. % of polyvinyl acetate, 25 to 40 wt. % of ethanol, 5 to 10 wt. % of polyvinyl pyrrolidone, and 25 to 35 wt. % of ethanol acetate. In the defined range of composition, it is possible not only to provide excellent adhesion with the hyaluronic acid-based dissolving film, making the release paper stick well to the film during and after production of the film, but also to ensure such a good detachability that the release paper can be easily removed by hand when being cut out.

As still further another example, the coating solution may preferably include 25 to 50 wt. % of polyvinyl acetate, 45 to 70 wt. % of ethanol, and 1 to 15 wt. % of polyvinyl pyrrolidone; and more preferably, 25 to 45 wt. % of polyvinyl acetate, 50 to 70 wt. % of ethanol, and 5 to 10 wt. % of polyvinyl pyrrolidone. In the defined range of composition, it is possible not only to provide excellent adhesion with the hyaluronic acid-based dissolving film, making the release liner stick well to the film during and after production of the film, but also to ensure such a good detachability that the release liner can be easily removed by hand when being cut out. It is more desirable in this case not to include ethyl acetate because of a beneficial effect to acquire far better adhesion and detachability.

The coating solution may further include, for example, at least one selected from the group consisting of dimethylformamide (DMF), methyl ethyl ketone (MEK), and polyvinyl alcohol.

The coating solution may be applied on the upper side of the release liner, for example, to a thickness of 10 to 100 μm, preferably 20 to 80 μm, and more preferably 20 to 60 μm, and then dried, for example, at 40 to 120° C., preferably 70 to 100° C. In the defined range of conditions, the manufactured hyaluronic acid-based dissolving film may display good mechanical properties.

The method may include, for example, kiss cutting the hyaluronic acid-based dissolving film after formation of the film. In this case, it facilitates the operation and use of the products and eliminates any waste in use to make an economic effect.

The term "kiss cutting" as used in the present invention is not specifically limited so long as it refers to method for making a kiss cut generally accepted in the related art of the present invention. And, it may mean, for example, cutting a portion of the hyaluronic acid-based film in advance in order to facilitate removal of the film in an appropriate amount or shape out of the release liner.

The method may further include, for example, supplying a mesh or a nonwoven fabric on the hyaluronic acid-based solution to form a continuous laminate, prior to drying the applied hyaluronic acid-based solution. In this case, it is easy to remove the solvent in the drying process, thus acquiring good appearance characteristics of the hyaluronic acid-based film. Even in the aspect of the features of the manufactured product, the hyaluronic acid-based dissolving film product can be put into contact at a desired position to dissolve the hyaluronic acid-based film and remove a mesh film, making it easy to use and advantageously maximizing the intended effect.

The method may further include, for example, removing the release paper after forming the hyaluronic acid-based dissolving film; preferably, removing the release paper so long as it includes supplying the mesh or nonwoven fabric to conduct a continuous lamination. This makes it easy to cut, store or transfer the manufactured hyaluronic acid-based dissolving film.

The method may further include, for example, winding the formed hyaluronic acid-based dissolving film. This facilitates the processing, storage, or transfer of the manufactured hyaluronic acid-based dissolving film.

The term "winding" as used in the present invention is not specifically limited so long as it is a word like "rolling" or "winding" that is used to mean rolling up into a scroll.

The hyaluronic acid-based solution may preferably include 10 to 33 wt. % of a hyaluronic acid-based compound, 50 to 90 wt. % of purified water, 0 to 3 wt. % of cellulose ether, 0 to 3 wt. % of polyvinyl alcohol, 0 to 1 wt. % of polyethylene glycol, and 0 to 10 wt. % of polyvinyl pyrrolidone; and more preferably, 15 to 28 wt. % of a hyaluronic acid-based compound, 62 to 84 wt. % of purified water, 0.1 to 1 wt. % of sodium carboxymethyl cellulose, 0 to 2 wt. % of polyvinyl alcohol, 0 to 1 wt. % of polyethylene glycol, and 0 to 7 wt. % of polyvinyl pyrrolidone. In the defined range of composition, it is possible to carry the hyaluronic acid-based dissolving film stably on the release liner of a continuous production line, ensuring a stable application of the solution and hence allowing a continuous production of the hyaluronic acid-based dissolving film.

The cellulose ether is preferably metallic carboxymethyl cellulose, and more preferably sodium carboxymethyl cellulose (CMC). This ensures a stable application of the solution and hence allows a continuous production of the hyaluronic acid-based dissolving film.

As another example, the hyaluronic acid-based solution may preferably include 15 to 30 wt. % of a hyaluronic acid-based compound, 0.1 to 1 wt. % of cellulose ether, 0 to 2 wt. % of polyvinyl alcohol, 0.1 to 1 wt. % of polyethylene glycol, 0 to 10 wt. % of polyvinyl pyrrolidone, and purified water for the balance; and more preferably, 18 to 26 wt. % of a hyaluronic acid-based compound, 0.2 to 0.6 wt. % of cellulose ether, 0.5 to 1.5 wt. % of polyvinyl alcohol, 0.2 to 0.6 wt. % of polyethylene glycol, 1 to 7 wt. % of polyvinyl pyrrolidone, and purified water for the balance. In the defined range of composition, it is possible not only to carry the hyaluronic acid-based dissolving film stably on the release paper of a continuous production line, allowing a mass production of the film, but also to acquire good properties in terms of both adhesion and detachability with the release paper.

The polyethylene glycol preferably includes at least one of PEG-40 hydrogenated castor oil and PEG-60 hydrogenated castor oil. In this case, it is possible to carry the film stably on the release liner of the continuous production line, acquire excellent properties in terms of both adhesion and detachability with the release liner and form little bubbles, so the hyaluronic acid-based dissolving film can display good appearance and physical characteristics.

The term "purified water" as used in the present invention includes distilled water or other water purified through an ion-exchange resin. It is not specifically limited so long as it refers to water generally accepted for use in the products in the related art of the present invention, even if not treated by distillation or purification.

The hyaluronic acid-based solution may be applied, for example, to a thickness of 80 to 180 μm and dried at 40 to 90° C. for 1 minute to 20 hours; and preferably, applied to a thickness of 80 to 120 μm and dried at 40 to 60° C. for 1 to 10 minutes. In the defined range of conditions, it is possible to achieve a mass production of the hyaluronic acid-based dissolving film with good properties in an economic manner.

The present invention also provides a hyaluronic acid-based dissolving film that includes: a sheet layer selected from a mesh, a nonwoven fabric, and a release liner; and a hyaluronic acid-based dissolving film layer adhered on the sheet layer. The mesh is selected from a nylon mesh, a PP mesh, and a PET mesh. The unwoven fabric is selected from a nylon unwoven fabric, a PP unwoven fabric, and a PET unwoven fabric. The release paper includes a coating layer formed on the one side or both sides of a film selected from a PET film, a corona treated PET film, an acrylic coated PET film, a silicon coated PET film, and an urethane coated PET film, where the coating layer includes at least one selected from the group consisting of polyvinyl alcohol, polyvinyl acetate, and polyvinyl pyrrolidone.

The term "nylon", "PP" or "PET" as used in the present invention is not specifically limited so long as it refers to nylon, a polypropylene (PP) resin or a polyethyleneterephthalate (PET) resin generally called in the related art of the present invention. It may include a copolymer further consisting of copolymerizable comonomers.

The film layer may be kisscut, for example. This facilitates the operation and use of the products and eliminates any waste in use, making an economic effect.

The coating layer may preferably include 70 to 95 wt. % of polyvinyl acetate and 5 to 30 wt. % of polyvinyl pyrrolidone; more preferably, 70 to 90 wt. % of polyvinyl acetate and 10 to 30 wt. % of polyvinyl pyrrolidone; and more preferably, 75 to 90 wt. % of polyvinyl acetate and 10 to 25 wt. % of polyvinyl pyrrolidone. In the defined range of composition, the hyaluronic acid-based dissolving film can be stably adhered to the release paper, causing no issue of inconvenience such as releasing flying powder during use, and easily removable from the release paper by hand when being cut out.

The film layer may preferably include a hyaluronic acid-based compound, cellulose ether, and polyethylene glycol. In this case, it dissolves well in contact with the skin or a solvent, such as water, cosmetic water, or ethanol, and does not inhibit the effects of compatible active ingredients, including antibacterial agents, herb extracts, or wound healing supplement agents.

More preferably, the film layer may include 90 to 98.5 wt. % of a hyaluronic acid-based compound, 1 to 5 wt. % of cellulose ether, and 0.5 to 5 wt. % of polyethylene glycol. In this case, it dissolves well in contact with the skin or a solvent, such as water, cosmetic water, or ethanol, and does not inhibit the effects of compatible active ingredients, including antibacterial agents, herb extracts, or wound healing supplement agents.

The film layer may further include, for example, at least one additive selected from the group consisting of a moisturizer, an antibacterial agent, a wound healing supplement agent, an absorption supplement agent, a plant-derived oil, a herb extract, an emulsion stabilizer, a film forming agent, a fragrance, a thickening agent, a skin conditioner, a binder, and an antioxidant in an amount of greater than 0 wt. % and less than 10 wt. %, preferably 0.5 to 5 wt. %, with respect to the total weight of the film layer. This allows the individual additives to make their effects without inhibiting the function of the hyaluronic acid-based compound.

For a specific example, the film layer may include 85 to 98.4 wt. % of a hyaluronic acid-based compound, 1 to 5 wt. % of cellulose ether, 0.5 to 5 wt. % of polyethylene glycol, and 0.1 to 5 wt. % of an additive; and preferably, 91 to 97.5 wt. % of a hyaluronic acid-based compound, 1 to 3 wt. % of cellulose ether, 0.5 to 3 wt. % of polyethylene glycol, and 1 to 3 wt. % of an additive. In this case, the film layer dissolves well in contact with the skin or a solvent, such as water, cosmetic water, or ethanol, and does not inhibit the inherent effects of the additives, such as antibacterial agents or wound healing supplement agents.

The film layer may have, for example, a viscosity (Brookfield rotary viscometer, room temperature, 50% Torque) of 3,000 to 7,000 cps, preferably 4,000 to 6,000 cps, and most preferably 4,400 to 5,600 cps. In the defined range of viscosity, the hyaluronic acid-based dissolving film can be stably adhered to the release paper, causing no issue of inconvenience such as releasing dusting powder during use, and easily removable from the release paper by hand when being cut out.

The film layer may have, for example, a strength (ASTM D638 standards, 5 mm/min) of 50 to 59 N/mm$^2$, preferably 53 to 58 N/mm$^2$. In the defined range of strength, the film layer can have good properties in terms of both adhesion and detachability with the hyaluronic acid-based film.

The mesh may have, for example, an opening size of 10 to 150 μm, preferably 40 to 100 μm. In the defined range of the opening size, there is no remains of the hyaluronic acid-based dissolving film left in the mesh pores when removing the mesh after the hyaluronic acid-based dissolving film adhered to the mesh is applied to the skin or the like; the customer satisfaction can be enhanced by allowing customers to see the hyaluronic acid-based film sticking to the skin or the like with naked eye; and high efficiency can be achieved because no additional process is required in using a continuous production line.

The term "mesh" as used in the present invention is not specifically limited so long as it refers to a mesh-like fabric, film, sheet, or the like generally defined in the related art of the present invention. Specific examples of the mesh may include fabrics, films, or sheets with dense pores like a mesh.

In the present invention, the opening size of the mesh, also called pore size, is defined as the internal linear distance between the two lines of a mesh without tension applied. For a specific example, the linear distance can be measured with a scanning electron microscope or an optical microscope.

The mesh may have, for example, a thickness of 100 to 500 μm, preferably 200 to 300 μm. In the defined range of thickness, there is no remains of the hyaluronic acid-based dissolving film left in the mesh pores when removing the mesh after the hyaluronic acid-based dissolving film adhered to the mesh is applied to the skin or the like; and high efficiency can be achieved because no additional process is required in using a continuous production line.

In the present invention, the thickness of the mesh can be measured, for example, with a scanning electron microscope, an optical microscope, or Vernier calipers.

The hyaluronic acid-based compound may have, for example, a weight average molecular weight of 4,000 to 1,500,000 g/mol, preferably 10,000 to 50,000 g/mol. In the defined range of the weight average molecular weight, the film dissolves well in contact with a solution, an emulsion, or the skin and does not inhibit the effects of compatible active ingredients, such as antibacterial agents, herb extracts, or wound healing supplement agents.

The hyaluronic acid-based dissolving film may be, for example, a product rolled up into a scroll alongside a release paper, a mesh, or a nonwoven fabric.

The present invention also provides a release liner that includes: a film layer; and an adhesive layer applied on the one side or both sides of the film layer by coating. The release liner has a lead content of 50 ppm or less and a cell viability (ISO 10993-5, based on negative control) of 90% or above. The film layer is selected from PET, corona treated PET, acrylic coated PET, silicon coated PET, and urethane coated PET. The adhesive layer includes 70 to 95 wt. % of polyvinyl acetate and 5 to 30 wt. % of polyvinyl pyrrolidone. Particularly when applied to the hyaluronic acid-based dissolving film, the release paper sticks well to the hyaluronic acid-based dissolving film during and after production of the film due to its good adhesion to the film and displays such a good detachability as to be easily removed by hand when being cut out.

The release paper has a lead content of 20 ppm or less and a cell viability (ISO 10993-5, based on negative control) of 95% or above. In this case, it can be harmless to human body, eco-friendly and excellent in adhesion to the hyaluronic acid-based film.

An application of the sheet by coating may not be specifically limited so long as it is conducted by a coating method generally used in the related art of the present invention.

According to the present invention, a hyaluronic acid-based solution, and a release paper suitable for a continuous film production process are developed, so it is possible to enable the production of a hyaluronic acid-based dissolving film with high performance in a fast and efficient way relative to the conventional production process such as solution casting or oven drying, allow mass production, and provide an advantage of making the hyaluronic acid-based dissolving film convenient in use.

BRIEF DESCRIPTION OF THE DRAWINGS

FIG. 1 is a mimetic diagram of a device for production of a hyaluronic acid-based dissolving film according to the present invention.

FIG. 2 is a mimetic diagram of a device for production of a release liner according to the present invention.

FIG. 5 presents photographic images of the test solutions containing eluates from the release liners of the present invention used and prepared in Examples, water for injection, and the standard lead solution (comparison solution), which were taken at the same time.

FIG. 6 is a graph showing the results of a cytotoxicity test for the test solutions and the comparison solution (ISO 10993-5, negative control).

DETAILED DESCRIPTION OF THE DISCLOSURE

Figure 3:
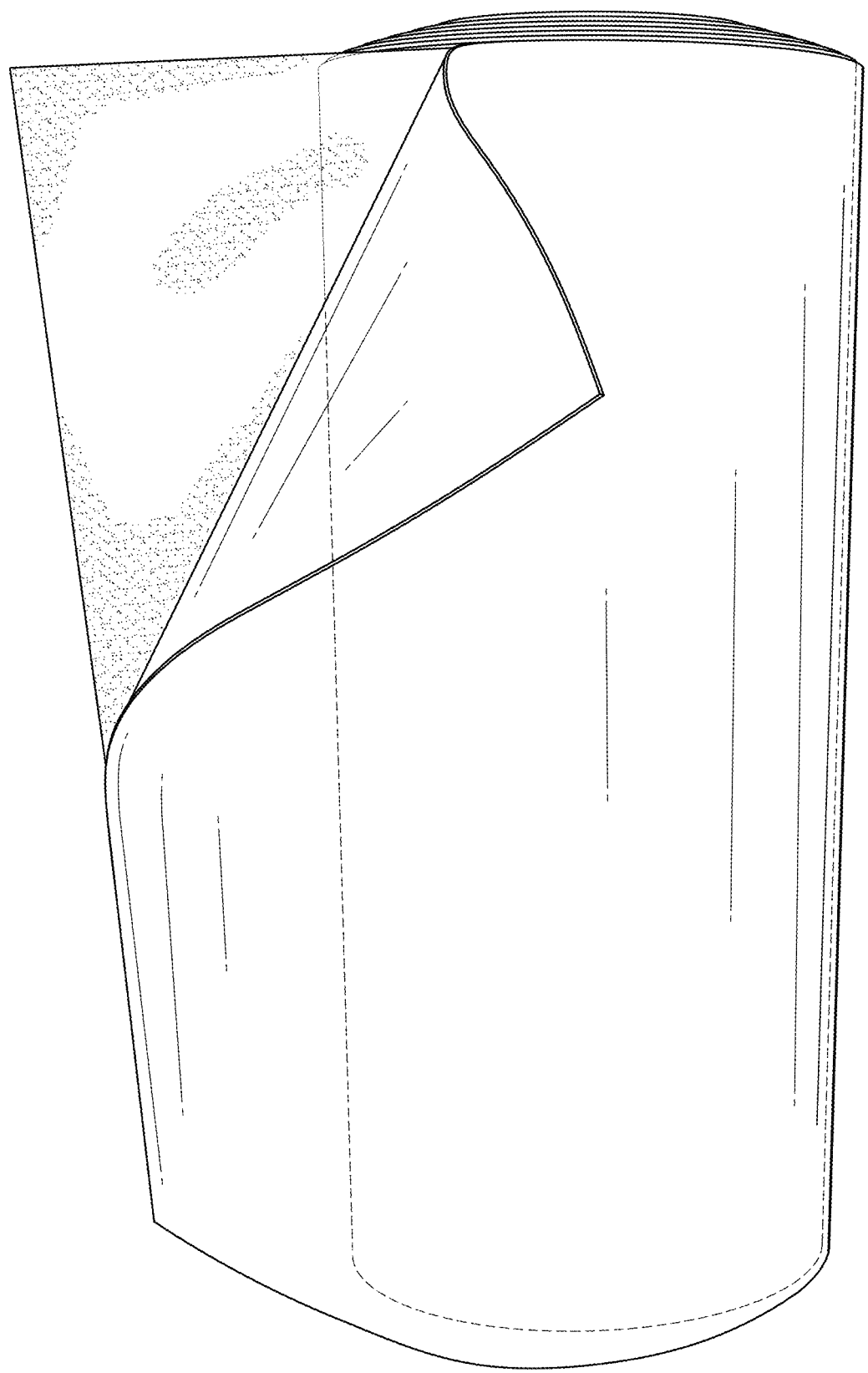
FIG. 3 is a photographic image showing the dissolving film of the present invention rolled up into a scroll after a continuous production line process.

Hereinafter, a detailed description will be given as to a method for producing a hyaluronic acid-based dissolving film according to the present invention.

The method for producing a hyaluronic acid-based dissolving film according to the present invention includes: preparing a hyaluronic acid-based solution capable of being carried on a continuous production line; continuously applying the hyaluronic acid-based solution to the upper side of a first release liner; and laminating and drying the applied hyaluronic acid-based solution, thereby providing the hyaluronic acid-based dissolution film with high productivity.

The hyaluronic acid-based solution includes, for example, 15 to 28 wt. % of a hyaluronic acid-based compound, 62 to 84 wt. % of purified water, 0.1 to 1 wt. % of sodium carboxymethyl cellulose, 1 to 2 wt. % of polyvinyl acetate (PVA), 0.1 to 1 wt. % of polyethylene glycol (PEG), and 1 to 7 wt. % of polyvinyl pyrrolidone (PVP). In the defined range of composition, a continuous film production process is enabled to provide a hyaluronic acid-based film with high productivity.

As another example, the hyaluronic acid-based solution includes 20 to 25 wt. % of a hyaluronic acid-based compound, 68 to 79 wt. % of purified water, 0.4 to 0.6 wt. % of sodium carboxymethyl cellulose, 1 to 2 wt. % of PVA, 0.3 to 0.6 wt. % of PEG, and 1 to 7 wt. % of PVP. In the defined range of composition, a continuous film production process is enabled to provide a hyaluronic acid-based film with high productivity.

As further another example, the hyaluronic acid-based solution includes 20 to 25 wt. % of a hyaluronic acid-based compound, 65 to 80 wt. % of purified water, 0.3 to 0.5 wt. % of sodium carboxymethyl cellulose, 0 to 1 wt. % of PVA, 0.2 to 0.4 wt. % of PEG, and 0 to 5 wt. % of PVP. In the defined range of composition, a continuous film production process is enabled to provide a hyaluronic acid-based film with high productivity.

The hyaluronic acid-based solution may further include an additive, such as skin cosmetic ingredients or wound healing ingredients, depending on the use purpose of the film product. For example, it may further include at least one additive selected from the group consisting of a moisturizer, an antibacterial agent, a wound healing supplement agent, an absorption supplement agent, a plant-derived oil, a herb extract, an emulsion stabilizer, a film forming agent, a fragrance, a thickening agent, a skin conditioner, a binder, and an antioxidant.

The additive may be included in an amount of greater than 0 wt. % and less than 10 wt. %, preferably 0.1 to 5 wt. %, and more preferably 0.3 to 1 wt. %, with respect to the total weight of the hyaluronic acid-based solution. In the defined range of the additive content, it is possible not only to achieve a continuous production of the film, but also to sufficiently provide the effects of the functional ingredients.

The hyaluronic acid-based compound may be, for example, hyaluronic acid, hyaluronate, or a mixture thereof.

The hyaluronate may include, for example, at least one selected from sodium hyaluronate, potassium hyaluronate, calcium hyaluronate, magnesium hyaluronate, zinc hyaluronate, cobalt hyaluronate, and tetrabutylammonium hyaluronate.

The hyaluronic acid-based compound may have, for example, a weight average molecular weight of 4,000 to 1,500,000 g/mol, 10,000 to 1,000,000 g/mol, 10,000 to 500,000 g/mol, or 10,000 to 15,000 g/mol. In the defined range of the weight average molecular weight, hyaluronic acid dissolves well in the solvent and causes neither stickiness nor residues, thereby providing high quality of the product and facilitating the production of films.

In the present invention, the weight average molecular weight of the hyaluronic acid-based compound is measured using gel permeation chromatography (GPC) with a solution prepared by dissolving the hyaluronic acid-based compound in pH-adjusted purified water. In this regard, the standard material is polyethylene oxide (PEO).

The hyaluronic acid-based solution is applied to the upper side of a first release liner. The first release liner may be a release liner selected from, for example, PET, corona treated PET alone, acryl coated PET, silicon coated PET, and urethane coated PET; and preferably selected from PET alone, corona treated PET, PET/PVac laminate, PET/PVP laminate, and PET/PVAc/PVP laminate. Most preferably, the first release liner is a PET-containing release liner in consideration of price and handleability.

The first release liner has, for example, a thickness of 70 to 200 μm, or 75 to 200 μm. In this case, it enables a continuous production process and ensures good handleability.

The hyaluronic acid-based solution may be applied, for example, to a thickness of 80 to 180 μm and dried at 40 to 90° C. for 1 minute to 2 hours.

As another example, the hyaluronic acid-based solution may be applied to a thickness of 100 to 150 μm and dried at 50 to 80° C. for 5 minutes or less, or 1 to 30 minutes. In the defined range of conditions, the production time is proper and the film does not undergo deformation.

The dried film may be rolled up into a scroll, for example, by means of a winding section.

The term "drying" as used in the present invention is not specifically limited so long as it is achieved by a method and/or device used in the related art of the present invention. It may include, for example, using heating rollers or a heating conveyor belt, hot air drying, or oven drying; preferably, oven drying or using a heating conveyor belt. In this case, drying uniformity and productivity are good.

The hyaluronic acid-based dissolving film may have, for example, a final thickness of 10 to 100 μm. In the defined range of the final thickness, the film does not tear easily and has good adhesion to the skin.

As a more specific example, the method for producing a hyaluronic acid-based dissolving film according to the present invention includes: preparing a hyaluronic acid-based solution; applying a first coating solution to the upper side of a first release liner and then drying the coating solution; continuously applying the hyaluronic acid-based solution to the upper side of the first release liner coated with the first coating solution; drying the applied hyaluronic acid-based solution; and kiss-cutting the dried film. In this case, it enables a continuous production of the hyaluronic acid-based film, providing high productivity, contributing to reduction of the production cost, and facilitating the handling and use of the product.

The first coating solution includes, for example, 10 to 30 wt. % of polyvinyl acetate, 20 to 40 wt. % of ethanol, 5 to 10 wt. % of polyvinyl pyrrolidone, and 0 to 30 wt. % of ethyl acetate. In this case, it ensures easy adhesion and detachment of the hyaluronic acid-based solution.

As another example, the first coating solution includes 20 to 40 wt. % of polyvinyl acetate, 20 to 30 wt. % of purified water, 30 to 50 wt. % of ethanol, and 1 to 5 wt. % of polyvinyl pyrrolidone. In this case, the hyaluronic acid-based solution easily adheres to the release liner during the processing step, and the hyaluronic acid-based dissolving film is easily removed in the use of the finished product, thereby securing convenience in use of the film.

The first coating solution is applied on the upper side of the first release liner, for example, to a thickness of 10 to 100 μm and dried at 40 to 120° C.

As another example, the first coating solution is applied on the upper side of the first release liner to a thickness of 20 to 80 μm and dried at 50 to 110° C.

Drying of the first coating solution is completed, for example, in 5 minutes, preferably in 3 minutes. This ensures good productivity.

The present invention provides a release liner that includes a film layer; and an adhesive layer applied on the one side or both sides of the film layer by coating. The sheet is selected from PET, corona treated PET, acrylic coated PET, silicon coated PET, and urethane coated PET. The adhesive layer includes 70 to 95 wt. % of polyvinyl acetate and 5 to 30 wt. % of polyvinyl pyrrolidone. The release liner sticks well to the hyaluronic acid-based dissolving film during and after production of the film due to its good adhesion to the film and displays good detachability so that it can be easily removed by hand when being cut out.

As another specific example, the method for producing a hyaluronic acid-based dissolving film according to the present invention includes: preparing a hyaluronic acid-based solution; continuously applying the hyaluronic acid-based solution to the upper side of a first release liner; continuously laying a second release liner over the applied hyaluronic acid-based solution; drying the laminated film; and removing the first release liner from the film and then winding the film. This enables a continuous production of the hyaluronic acid-based film, which eventually provides high productivity, contributes to reduction of the production cost, and facilitates the handling and use of the product.

The second release liner may be selected from a nonwoven fabric, or a mesh made of a variety of materials, for example, PET, PP, or PE. Preferably, it may be selected from a nylon mesh, a PP mesh, and a PET mesh. The desirable second release liner is a PET mesh in the aspect of production on a continuous line or ease of handling; or a nylon mesh in the aspect of price or ease of use due to its soft texture.

Preferably, the mesh has a thickness of 200 to 300 μm and an opening size of 10 to 100 μm. In this case, the product can be provided with high production and favorably convenient to use.

Hereinafter, a description will be given as to the method for producing a hyaluronic acid-based dissolving film according to the present invention with reference to the accompanying drawings. FIG. 1 is a mimetic diagram showing a device for producing the hyaluronic acid-based dissolving film of the present invention. Referring to FIG. 1, the hyaluronic acid-based dissolving film of the present invention is manufactured by a method that includes: preparing a hyaluronic acid-based solution; applying the hyaluronic acid-based solution to the upper side of a first release liner through a stationary application section; optionally laying a second release liner over the selectively applied hyaluronic acid-based solution; and passing the film through a drying chamber for lamination and drying.

After application, the hyaluronic acid-based solution may be cut to a desired thickness with a cutter.

Lamination and drying is conducted in the first drying chamber. The drying chamber may include a plurality of drying chambers, preferably 5 to 10 drying chambers, which are arranged in a row. The individual drying chambers may have different temperatures. This can raise the drying temperature gradually to minimize deformation or destruction of the hyaluronic acid-based dissolving film by heat.

After passing through the drying chambers, the film is removed of the first release liner and then completed through a winding section (not shown). The winding section is not specifically limited so long as it is a winding means generally used in the related art of the present invention, and it may be, for example, a winding device for rolling up the film into a scroll.

The device for producing a hyaluronic acid-based dissolving film as shown in FIG. 1 can also be used as a device for producing a release liner according to the present invention as shown in FIG. 2. In this case, the above-described film is used in place of the first release liner and the above-described coating solution is applied to a solution dispenser, lamination with the second release liner is skipped. This makes it possible to produce the release liner of the present invention with ease.

If not further shown, when the device for producing a hyaluronic acid-based dissolving film in FIG. 1 and the device for producing a release liner according to the present invention in FIG. 2 are connected in series to each other, it is possible to conduct a continuous process from the production of the release liner of the present invention to the production of the hyaluronic acid-based dissolving film of the present invention in the order of film→solution dispense (coating solution)→cutter→drying chamber→solution dispense (hyaluronic acid-based solution)→cutter→(optionally, laminating with the second release liner)→drying chamber→the finished product.

FIG. 3 is a photographic image showing the dissolving film of the present invention rolled up into a scroll after a continuous production line process. The hyaluronic acid-based dissolving film is stably adhered to the finished product, making it possible to visually confirm good adhesion. In addition, the release liner can be easily removed from the actual film, confirming good detachability. Further, the detached hyaluronic acid-based dissolving film is intact in shape and clear, showing that the prepared hyaluronic acid-based dissolving film is excellent in physical properties and appearance.

Figure 4:
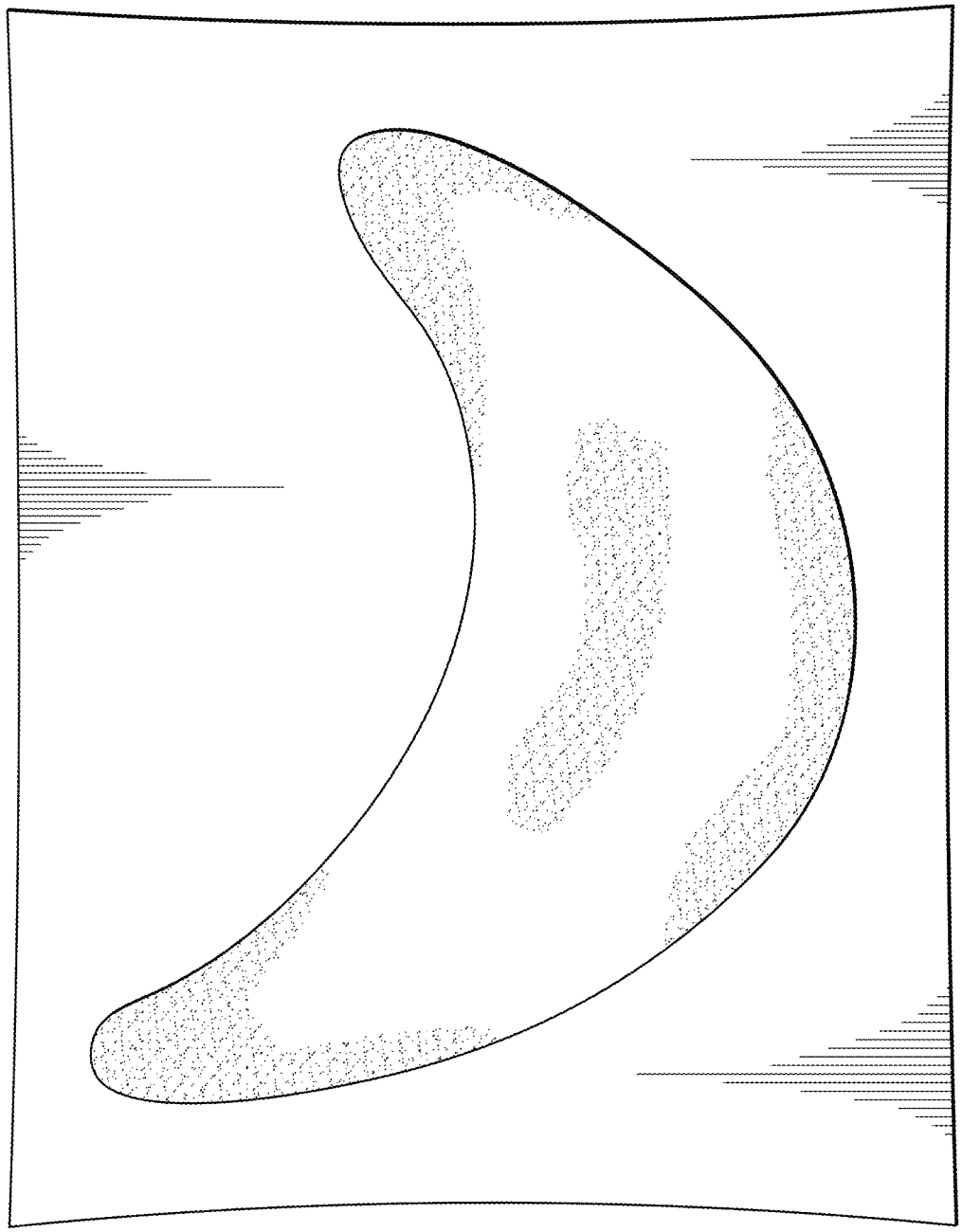
FIG. 4 is a photographic image showing the hyaluronic acid-based dissolving film which has a kiss cut.

FIG. 4 is a photographic image showing the hyaluronic acid-based dissolving film of the present invention that has a kiss cut. The hyaluronic acid-based dissolving film has the kiss cut in a half-moon shape on the release liner, so the half-moon-shaped dissolving film can be removed from the release liner and used appropriately.

Hereinafter, preferred embodiments will be given for better understanding of the present invention. The following examples are given only for illustration of the present invention and subject to many modifications and variations, which of course belong to the claims of the present invention.

EXAMPLES

Example 1

Preparation of Hyaluronic Acid Solution

A hyaluronic acid solution was prepared to have a composition including 20 wt. % of hyaluronic acid having a weight average molecular weight of 11,000 g/mol, 0.4 wt. % of sodium carboxymethyl cellulose, 0.25 wt. % of polyethylene glycol, 0.1 wt. % of an herb extract, and purified water for the balance.

Preparation of Dissolving Film

A PET film having a thickness of 100 μm was prepared as a release liner and supplied to the continuous production line as shown in FIG. 2. A coating solution containing 40 wt. % of ethanol, 22 wt. % of purified water, 30 wt. % of polyvinyl acetate, and 8 wt. % of polyvinyl pyrrolidone was applied to a thickness of 40 μm on the upper side of the release liner, followed by drying at 90° C. for 2 minutes in a drying chamber to conduct a coating process. Subsequently, the coated release liner was supplied to the continuous production line of FIG. 1. The hyaluronic acid-based solution prepared above was applied to a thickness of 100 μm on the upper side of the coated release liner, followed by drying at 50° C. for 3 minutes in the drying chamber and winding to make a hyaluronic acid-based dissolving film. Here, laminating with a second release liner was skipped.

Example 2

Preparation of Hyaluronic Acid Solution

A hyaluronic acid solution was prepared to have a composition including 25 wt. % of hyaluronic acid having a weight average molecular weight of 11,000 g/mol, 0.5 wt. % of sodium carboxymethyl cellulose, 1 wt. % of polyvinyl alcohol, 5 wt. % of polyvinyl pyrrolidone, 0.5 wt. % of polyethylene glycol, and purified water for the balance.

Preparation of Dissolving Film

The procedures were performed to prepare a hyaluronic acid-based dissolving film in the same manner as described in Example 1, excepting that the hyaluronic acid solution of the above composition was used.

Example 3

Preparation of Hyaluronic Acid Solution

A hyaluronic acid solution was prepared to have a composition including 19 wt. % of hyaluronic acid having a weight average molecular weight of 11,000 g/mol, 0.37 wt. % of sodium carboxymethyl cellulose, 0.75 wt. % of polyvinyl alcohol, 3.7 wt. % of polyvinyl pyrrolidone, 0.37 wt. % of polyethylene glycol, and purified water for the balance.

Preparation of Dissolving Film

The procedures were performed to prepare a hyaluronic acid-based dissolving film in the same manner as described in Example 1, excepting that the hyaluronic acid solution of the above composition was used.

Example 4

Preparation of Hyaluronic Acid Solution

A hyaluronic acid solution was prepared with the same composition of Example 1.

Preparation of Dissolving Film

The above-prepared hyaluronic acid solution was applied to a thickness of 100 μm on the upper side of the release liner coated in the same manner as described in Example 1. Then, a nylon mesh as a second release liner was put down in the sections for laminating with the second release liner as shown in FIG. 1. The laminate was dried out at 50° C. for 3 minutes in a drying chamber, and then rolled up with or without removal of the coated release liner to complete a hyaluronic acid-based dissolving film.

Example 5

The procedures were performed to prepare a hyaluronic acid-based dissolving film in the same manner as described in Example 1, excepting that the step of coating the release liner with the coating solution was skipped.

Example 6

The procedures were performed to prepare a hyaluronic acid-based dissolving film in the same manner as described in Example 4, excepting that the step of coating the release liner with the coating solution was skipped.

Example 7

The procedures were performed to prepare a hyaluronic acid-based dissolving film in the same manner as described in Example 1, excepting that the coating solution was composed of 40 wt. % of ethanol, 22 wt. % of ethyl acetate, 30 wt. % of polyvinyl acetate, and 8 wt. % of polyvinyl pyrrolidone.

Reference Example 1

Preparation of Hyaluronic Acid Solution

A hyaluronic acid solution was prepared to have a composition including 20 wt. % of hyaluronic acid having a weight average molecular weight of 11,000 g/mol, 2 wt. % of polyvinyl alcohol, 1 wt. % of polyethylene glycol, and purified water for the balance.

Preparation of Dissolving Film

The procedures were performed to prepare a hyaluronic acid-based dissolving film in the same manner as described in Example 1, excepting that the hyaluronic acid solution of the above composition was used.

Reference Example 2

Preparation of Hyaluronic Acid Solution

A hyaluronic acid solution was prepared to have a composition including 30 wt. % of hyaluronic acid having a weight average molecular weight of 11,000 g/mol, 2 wt. % of pullulan, 0.5 wt. % of sodium carboxymethyl cellulose, 1 wt. % of polyvinyl alcohol, 5 wt. % of polyvinyl pyrrolidone, 0.5 wt. % of polyethylene glycol, and purified water for the balance.

Preparation of Dissolving Film

The procedures were performed to prepare a hyaluronic acid-based dissolving film in the same manner as described in Example 1, excepting that the hyaluronic acid solution of the above composition was used.

Reference Example 3

Preparation of Hyaluronic Acid Solution

A hyaluronic acid solution was prepared to have a composition including 25 wt. % of hyaluronic acid having a weight average molecular weight of 11,000 g/mol, 0.5 wt. % of hyaluronic acid having a weight average molecular weight of 1,350,000 g/mol, 0.5 wt. % of sodium carboxymethyl cellulose, 1 wt. % of polyvinyl alcohol, 5 wt. % of polyvinyl pyrrolidone, 0.5 wt. % of polyethylene glycol, and purified water for the balance.

Preparation of Dissolving Film

The procedures were performed to prepare a hyaluronic acid-based dissolving film in the same manner as described in Example 1, excepting that the hyaluronic acid solution of the above composition was used.

Reference Example 4

Preparation of Hyaluronic Acid Solution

A hyaluronic acid solution was prepared to have a composition including 0.9 wt. % of hyaluronic acid having a weight average molecular weight of 11,000 g/mol, 0.1 wt. % of hyaluronic acid having a weight average molecular weight of 1,350,000 g/mol, and purified water for the balance.

Preparation of Dissolving Film

The above-prepared hyaluronic acid solution was dispensed on a square polyethylene dish and dried in an oven at 50° C. for 12 hours to prepare a hyaluronic acid-based dissolving film.

Comparative Example 1

Preparation of Hyaluronic Acid Solution

A hyaluronic acid solution was prepared to have a composition including 1.6 wt. % of hyaluronic acid having a weight average molecular weight of 11,000 g/mol, 0.4 wt. % of polyvinyl alcohol, and purified water for the balance.

Preparation of Dissolving Film

The above-prepared hyaluronic acid solution was dispensed on a square polyethylene dish and dried in an oven at 50° C. for 12 hours to prepare a hyaluronic acid-based dissolving film.

Comparative Example 2

Preparation of Hyaluronic Acid Solution

A hyaluronic acid solution was prepared to have a composition including 1.6 wt. % of hyaluronic acid having a weight average molecular weight of 1,350,000 g/mol, 0.4 wt. % of polyvinyl alcohol, and purified water for the balance.

Preparation of Dissolving Film

The above-prepared hyaluronic acid solution was dispensed on a square polyethylene dish and dried in an oven at 50° C. for 12 hours to prepare a hyaluronic acid-based dissolving film.

Reference Example 5

The procedures were performed to prepare a dissolving film in the same manner as described in Example 1, excepting that the composition of the coating solution included 45 wt. % of purified water and 55 wt. % of polyvinyl acetate.

Testing Example 1

The following methods were employed to measure the toxicity of the substances eluted from the release liners used or coated in the Examples, Comparative Examples and Reference Examples. The measurement results are presented in FIGS. 5 and 6.

Heavy metal test: The test solution was prepared by placing 10 ml of each sample solution (an eluate from the release liner) and adding 2 ml of diluted acetic acid and water to make 50 ml. The comparison solution was prepared by placing 2 ml of the lead standard solution and adding 2 ml of diluted acetic acid and water to make 50 ml (lead, 20 ppm). One drop of a sodium sulfide reagent was added to the test solution and comparison solution respectively. The test solution and comparison solution were left for 5 minutes and subjected to a visual evaluation (according to Method 1, Heavy Metal Test Methods, General Test Methods of the Korean Pharmacopoeia).

Cytotoxicity test: A cell suspension containing L-929 fibroblast cells ($1\times10^5$ cells/ml ratio) was dispensed in a 6-well plate at a rate of 2 ml/well and cultured for 24 hours. The test solution and comparison solution were prepared from the cell suspension and cultured for 24 hours. Then, the number of living cell colonies was counted to evaluate the cytotoxicity (according to ISO 10993-5, Biological evaluation of medical devices—Part 5: Tests for in vitro cytotoxicity).

Drying time: The length of time required from the application of each hyaluronic acid solution on the release liner to the complete drying (no change in weight) of the solution at 50° C. was measured.

Adhesion to the release liner: Before the winding of each dissolving film, adhesion of the release liner and the dissolving film was visually evaluated in terms of O/X.

Detachability of the dissolving film after processing: Before the winding of each dissolving film, the dissolving film was removed from the release liner by hand to evaluate the detachability.

Dissolution of the dissolving film: A certain amount of water was applied to each of the above-prepared dissolving films to visually evaluate whether the film dissolved in one second, in terms of O/X.

Strength: According to the ASTM D638 standards, each of the above-prepared dissolving films was cut into a sample in the shape of a dog bone and subjected to a tensile strength test at a rate of 5 mm/min to evaluate the strength.

In the case of the test methods associated with visual evaluation, the evaluation results are presented in Tables 1 and 2, where the symbol "O" indicates the results satisfactory or passing the standards; and the symbol "X" indicates the results dissatisfactory or not passing the standards, or immeasurable.

TABLE 1

| | Example | | | Comparative Example | | | | Reference Example | |
|---|---|---|---|---|---|---|---|---|---|
| Div. | 1 | 2 | 3 | 1 | 2 | 3 | 4 | 1 | 2 |
| Dissolution | O | O | O | O | X | X | O | O | O |
| Viscosity (cps) | 4,440 | 5,270 | 5,560 | 3,500 | 6,900 | 7,360 | 340 | 300 | 410 |
| Film formation | O | O | O | O | O | O | O | O | X |
| Drying time | 3 min or less | 5 min or less | 3 min or less | 5 min or less | 5 min or less | 5 min or less | 12 hrs | 12 hrs | 12 hrs |
| Adhesion to first release liner | O | O | O | X | X | X | — | — | — |
| Detachability of dissolving film after processing | O | O | O | * | * | * | — | — | — |
| Dissolution of hyaluronic acid-based film | O | O | O | O | — | — | X | O | O |
| Strength (N/mm$^2$) | 53.6 | 56.4 | 57.8 | 48.3 | 60.2 | 60.6 | 30.7 | 38.3 | — |

* The dissolving film is detached during processing.

Testing Example 2

The following methods were employed to measure the characteristics of the hyaluronic acid-based dissolving films prepared in Examples 1 to 7, Comparative Examples 1 and 2, and Reference Examples 1 to 5. The results are presented in Tables 1 and 2 as follows.

Dissolution: The above-prepared solutions were visually observed in regards to the residual ingredients, agglomeration or phase separation to evaluate the dissolution in terms of O/X.

Viscosity: The viscosity at room temperature and 50% torque was measured with a Brookfield rotational viscometer.

Formation of films: The above-prepared hyaluronic acid solutions were applied on the release liner, dried out completely, and visually observed to determine the film formation of the solutions in terms of O/X.

TABLE 2

| Div. | Example 4 | Example 5 | Example 6 | Example 7 | Reference Example 5 |
|---|---|---|---|---|---|
| Film formation | O | O | O | O | O |
| Drying time | 3 min or less | 3 min or less | 3 min or less | 3 min or less | 3 min or less |
| Adhesion to first release liner | O | X | X | O | O |
| Detachability of dissolving film after processing | O | — | — | O | X |
| Dissolution of hyaluronic acid-based film | O | O | O | O | — |

As can be seen from FIG. 5, the results of the heavy metal test for lead, water for injection, a release liner, and a release liner coated with the coating solution (hereinafter, referred to as "coated release liner") are those for an aqueous solution of 20 ppm lead, water for injection, the eluate of the release liner before coating, and the eluate of the coated release liner, respectively. The eluates of the release liner and the coated release liner according to the present invention were not deeper in color than the comparison solution, that is, they contained 20 ppm or less of heavy metals, and then contained less heavy metals than the comparison solution contained. It claimed that the elutes of the coated film according to the present invention were safe. The elutes of the release liner and the coated release liner according to the present invention also met the requirement that they should not be darker in color than the comparison solution (lead, 20 ppm), according to Method 1, Heavy Metal Test Methods, General Test Methods of the Korean Pharmacopoeia.

As can be seen from FIG. 6, the results of the cytotoxicity test showed that the elutes of the release liner before coating and the coated release liner had the cell viability of 97.79±0.76% and 96.24±1.09%, respectively, based on the negative control described in ISO 10993-5. According to the table of Qualitative Morphological Grading of Cytotoxicity of Extracts (ISO 10993-5), the elutes of the release liner before coating and the coated release liner according to the present invention showed cytotoxicity indicated by "grade 0" and proved to be safe.

As shown in Table 1, the hyaluronic acid-based dissolving films of the present invention (Examples 1 to 4) displayed superiority in all the properties to the comparative examples, allowed a continuous production with high efficiency, caused neither dusting powder nor unexpected break by stably sticking to the release liner, thereby providing convenience in use, and economical efficiency, and had good detachability after processing and good dissolution properties.

As shown in Table 2, the hyaluronic acid-based dissolving films of the present invention (Examples 4 to 7) were available in mass production by using a coated release liner, which contributed to much improved adhesion and detachability after processing. Particularly, the hyaluronic acid-based dissolving film including the second release liner according to the present invention (Example 4) enabled fast production of hyaluronic acid-based dissolving films with high performance, displayed excellences in both adhesion and detachability, and provided convenience in use thanks to using the second release liner as described above.

What is claimed is:

1. A continuous production method for a hyaluronic acid-based dissolving film, comprising:
    preparing a hyaluronic acid-based solution capable of being carried on a continuous production line;
    supplying a release paper to the continuous production line;
    continuously applying the hyaluronic acid-based solution on the upper side of a release liner supplied to the continuous production line;
    drying the applied hyaluronic acid-based solution on the continuous production line to form a hyaluronic acid-based dissolving film; and
    applying a coating solution on the upper side of the release paper and then drying the applied coating solution prior to or after supplying the release paper to the continuous production line,
    wherein the coating solution comprises 10 to 20 wt. % of polyvinyl acetate, 10 to 20 wt. % of water, 50 to 70 wt. % of ethanol, and 1 to 10 wt. % of polyvinyl pyrrolidone,
    wherein the hyaluronic acid-based solution comprises 18 to 26 wt. % of a hyaluronic acid-based compound, 0.2 to 0.6 wt. % of cellulose ether, 0.5 to 1.5 wt. % of polyvinyl alcohol, 0.2 to 0.6 wt. % of polyethylene glycol, 1 to 7 wt. % of polyvinyl pyrrolidone, and
    wherein the hyaluronic acid-based compound has a weight average molecular weight of 10,000 to 50,000 g/mol.

2. The production method according to claim 1, further comprising:
    kiss-cutting the hyaluronic acid-based dissolving film after formation of the film.

3. The production method according to claim 1, further comprising:
    supplying a mesh or a nonwoven fabric on the hyaluronic acid-based solution to conduct a continuous lamination, prior to drying the applied hyaluronic acid-based solution.

4. The production method according to claim 1, further comprising:
    removing the release paper after forming the hyaluronic acid-based dissolving film.

5. The production method according to claim 1, further comprising:
    winding the formed hyaluronic acid-based dissolving film.

6. The production method according to claim 1, wherein the hyaluronic acid-based solution is applied to a thickness of 80 to 180 μm and dried at 40 to 90° C. for 1 minute to 2 hours.

* * * * *